(12) United States Patent
Verseck et al.

(10) Patent No.: US 6,372,459 B1
(45) Date of Patent: Apr. 16, 2002

(54) N-ACETYL AMINO ACID RACEMASE

(75) Inventors: Stefan Verseck, Aachen; Maria-Regina Kula, Niederzier; Andreas Bommarius, Frankfurt am Main; Karlheinz Drauz, Freigericht, all of (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/624,390

(22) Filed: Jul. 27, 2000

(30) Foreign Application Priority Data

Jul. 27, 1999 (DE) .......................... 199 35 268

(51) Int. Cl.[7] .......................... C12P 13/04; C12N 9/90; C12N 1/20; C12N 15/00; C07H 21/04

(52) U.S. Cl. ................ 435/106; 435/233; 435/252.3; 435/320.1; 536/23.2; 530/350

(58) Field of Search ................................. 435/106, 233, 435/252.3, 320.1; 536/23.2; 530/350

(56) References Cited

FOREIGN PATENT DOCUMENTS

| EP | 0 304 021 | 2/1989 |
| EP | 0 474 965 | 3/1992 |

OTHER PUBLICATIONS

S. Tokuyama, et al., Database EMBL Sequence Database, pp. 1–8, AN D30738, "Amycolatopsis SP. AAAR Gene for M–Acelamino Acid Racemase, Complete AAR; N–Acylamino Acid Racemase", Oct. 4, 1995.

C.G. Marshall, et al., Antimicrobial Agents and Chemotherapy, vol. 42, No. 9, pp. 2215–2220, "Glycopeptide Antibiotic Resistance Genes In Glycopeptide–Producing Organisms", 1998.

Annette Mehling, et al., Database BIOSIS 'Online' Biosciences Information Service, vol. 141, No. 9, 1 page, "Nucleotide Sequences of Streptomycete 16S Ribosomal DNA: Towards a Specific Identification System for Streptomycetes Using PCR", 1995.

*Primary Examiner*—Ponnathapu Achutamurthy
*Assistant Examiner*—Tekchand Saidha
(74) *Attorney, Agent, or Firm*—Oblon, Spivak, McClelland, Maier & Neustadt, P.C.

(57) ABSTRACT

The present invention is directed to an N-acetyl amino acid racemase (AAR) as well as the gene coding for it, to a plasmid, vector and microorganism containing the gene. A method of producing enantiomer-enriched amino acids, and derivatives thereof, is also provided.

5 Claims, 5 Drawing Sheets

SEQUENCE LISTING

<160> NUMBER OF SEQ ID NOS: 7

<210> SEQ ID NO 1
<211> LENGTH: 1107
<212> TYPE: DNA
<213> ORGANISM: Amycolatopsis orientalis
<220> FEATURE:
<221> NAME/KEY: CDS
<222> LOCATION: (1)..(1107)

<400> SEQUENCE: 1

```
gtg aaa ctc agc ggt gtg gaa ctg cgc cgg gtc cgg atg ccg ctc gtg      48
Val Lys Leu Ser Gly Val Glu Leu Arg Arg Val Arg Met Pro Leu Val
 1               5                  10                  15 gcc ccg ttc cgg acg tcg ttc ggg acg cag tcc gag cgg gaa ttg ctg      96
Ala Pro Phe Arg Thr Ser Phe Gly Thr Gln Ser Glu Arg Glu Leu Leu
             20                  25                  30 ctg gtc cgc gcg gtg acc ccg gcg ggc gag ggc tgg ggc gaa tgt gtc     144
Leu Val Arg Ala Val Thr Pro Ala Gly Glu Gly Trp Gly Glu Cys Val
         35                  40                  45 gcg atg gag gcg ccg ctc tac tcg tcg gag tac aac gac gcc gcc gag     192
Ala Met Glu Ala Pro Leu Tyr Ser Ser Glu Tyr Asn Asp Ala Ala Glu
     50                  55                  60 cac gtg ctg cgg aac cat ctg atc ccc gca ctg ctg gcg gcc gag gac     240
His Val Leu Arg Asn His Leu Ile Pro Ala Leu Leu Ala Ala Glu Asp
 65                  70                  75                  80 gtg acc gcg cac aag gtg acg ccg ttg ctg gcg aag ttc aag ggc cac     288
Val Thr Ala His Lys Val Thr Pro Leu Leu Ala Lys Phe Lys Gly His
                 85                  90                  95 cgg atg gcg aag ggc gcg ctg gag atg gcg gtc ctc gac gcc gaa ctc     336
```

```
                                                                                -continued Arg Met Ala Lys Gly Ala Leu Glu Met Ala Val Leu Asp Ala Glu Leu
                100                 105                 110 cgc gcg cat gac cgg tcc ttc gcg gcc gag ctg ggg tcc act cgc gac       384
Arg Ala His Asp Arg Ser Phe Ala Ala Glu Leu Gly Ser Thr Arg Asp
            115                 120                 125 tcc gtg gcc tgc ggg gtc tcg gtc ggg atc atg gac tcg atc ccg cac       432
Ser Val Ala Cys Gly Val Ser Val Gly Ile Met Asp Ser Ile Pro His
        130                 135                 140 ctg ctc gac gtc gtc ggc ggc tac ctc gac gag ggc tac gtc cgg atc       480
Leu Leu Asp Val Val Gly Gly Tyr Leu Asp Glu Gly Tyr Val Arg Ile
145                 150                 155                 160 aag ctg aag atc gag ccc ggc tgg gac gtc gag ccg gtc cgg cag gtg       528
Lys Leu Lys Ile Glu Pro Gly Trp Asp Val Glu Pro Val Arg Gln Val
                165                 170                 175 cgt gag cgc ttc ggt gac gac gtg ctg ctg cag gtc gac gcg aac acc       576
Arg Glu Arg Phe Gly Asp Asp Val Leu Leu Gln Val Asp Ala Asn Thr
            180                 185                 190 gcg tac acg ctg ggc gac gcg ccc ctg ctg tcc cgg ctc gac ccg ttc       624
Ala Tyr Thr Leu Gly Asp Ala Pro Leu Leu Ser Arg Leu Asp Pro Phe
        195                 200                 205 gac ctg ctg ctg atc gag cag ccg ctc gaa gaa gag gac gtg ctc ggc       672
Asp Leu Leu Leu Ile Glu Gln Pro Leu Glu Glu Glu Asp Val Leu Gly
210                 215                 220 cac gcc gag ctg gcc aag cgg atc cgg acg ccg atc tgc ctc gac gag       720
His Ala Glu Leu Ala Lys Arg Ile Arg Thr Pro Ile Cys Leu Asp Glu
225                 230                 235                 240 tcg atc gtc tcg gcc aag gcc gcc gcg gac gcg atc aag ctc ggc gcc       768
Ser Ile Val Ser Ala Lys Ala Ala Ala Asp Ala Ile Lys Leu Gly Ala
                245                 250                 255 tgc cag atc gtc aac atc aaa ccg ggc cgg gtc ggc gga tac ctc gaa       816
Cys Gln Ile Val Asn Ile Lys Pro Gly Arg Val Gly Gly Tyr Leu Glu
            260                 265                 270 gcc cgc cgg gtg cac gac gtc tgc gcg gca cac ggg atc gcg gtg tgg       864
Ala Arg Arg Val His Asp Val Cys Ala Ala His Gly Ile Ala Val Trp
        275                 280                 285 tgc ggc ggg atg atc gag acc ggg ctc ggc cgg gcg gcc aac gtc gca       912
Cys Gly Gly Met Ile Glu Thr Gly Leu Gly Arg Ala Ala Asn Val Ala
    290                 295                 300 ctg gcc tcg ctg ccc ggc ttc acg ctg ccg ggg gac acc tcg gcg tcc       960
Leu Ala Ser Leu Pro Gly Phe Thr Leu Pro Gly Asp Thr Ser Ala Ser
305                 310                 315                 320 ggc cgg ttc tat cgc acc gac atc acc gag ccg ttc gtg ctg gac gcc      1008
Gly Arg Phe Tyr Arg Thr Asp Ile Thr Glu Pro Phe Val Leu Asp Ala
                325                 330                 335 ggg cat ctg ccg gtg ccg acc ggg ccg ggc ctc ggg gtg act ccg att      1056
Gly His Leu Pro Val Pro Thr Gly Pro Gly Leu Gly Val Thr Pro Ile
            340                 345                 350 ccg gat ctt ctg gac gag gtc acc acg gag aaa gcg tgg atc ggt tcg      1104
Pro Asp Leu Leu Asp Glu Val Thr Thr Glu Lys Ala Trp Ile Gly Ser
        355                 360                 365 tag                                                                   1107

210> SEQ ID NO 2
<211> LENGTH: 368
<212> TYPE: PRT
<213> ORGANISM: Amycolatopsis orientalis

<400> SEQUENCE: 2

Val Lys Leu Ser Gly Val Glu Leu Arg Arg Val Arg Met Pro Leu Val
 1               5                  10                  15
```

```
Ala Pro Phe Arg Thr Ser Phe Gly Thr Gln Ser Glu Arg Glu Leu Leu
         20                  25                  30

Leu Val Arg Ala Val Thr Pro Ala Gly Glu Gly Trp Gly Glu Cys Val
         35                  40                  45

Ala Met Glu Ala Pro Leu Tyr Ser Ser Glu Tyr Asn Asp Ala Ala Glu
         50                  55                  60

His Val Leu Arg Asn His Leu Ile Pro Ala Leu Leu Ala Ala Glu Asp
 65                  70                  75                  80

Val Thr Ala His Lys Val Thr Pro Leu Leu Ala Lys Phe Lys Gly His
                 85                  90                  95

Arg Met Ala Lys Gly Ala Leu Glu Met Ala Val Leu Asp Ala Glu Leu
                100                 105                 110

Arg Ala His Asp Arg Ser Phe Ala Ala Glu Leu Gly Ser Thr Arg Asp
             115                 120                 125

Ser Val Ala Cys Gly Val Ser Val Gly Ile Met Asp Ser Ile Pro His
         130                 135                 140

Leu Leu Asp Val Val Gly Gly Tyr Leu Asp Glu Gly Tyr Val Arg Ile
145                 150                 155                 160

Lys Leu Lys Ile Glu Pro Gly Trp Asp Val Glu Pro Val Arg Gln Val
                165                 170                 175

Arg Glu Arg Phe Gly Asp Asp Val Leu Leu Gln Val Asp Ala Asn Thr
            180                 185                 190

Ala Tyr Thr Leu Gly Asp Ala Pro Leu Leu Ser Arg Leu Asp Pro Phe
        195                 200                 205

Asp Leu Leu Leu Ile Glu Gln Pro Leu Glu Glu Asp Val Leu Gly
    210                 215                 220

His Ala Glu Leu Ala Lys Arg Ile Arg Thr Pro Ile Cys Leu Asp Glu
225                 230                 235                 240

Ser Ile Val Ser Ala Lys Ala Ala Asp Ala Ile Lys Leu Gly Ala
                245                 250                 255

Cys Gln Ile Val Asn Ile Lys Pro Gly Arg Val Gly Gly Tyr Leu Glu
            260                 265                 270

Ala Arg Arg Val His Asp Val Cys Ala Ala His Gly Ile Ala Val Trp
        275                 280                 285

Cys Gly Gly Met Ile Glu Thr Gly Leu Gly Arg Ala Ala Asn Val Ala
    290                 295                 300

Leu Ala Ser Leu Pro Gly Phe Thr Leu Pro Gly Asp Thr Ser Ala Ser
305                 310                 315                 320

Gly Arg Phe Tyr Arg Thr Asp Ile Thr Glu Pro Phe Val Leu Asp Ala
                325                 330                 335

Gly His Leu Pro Val Pro Thr Gly Pro Gly Leu Gly Val Thr Pro Ile
            340                 345                 350

Pro Asp Leu Leu Asp Glu Val Thr Glu Lys Ala Trp Ile Gly Ser
        355                 360                 365

<210> SEQ ID NO 3
<211> LENGTH: 504
<212> TYPE: DNA
<213> ORGANISM: Amycolatopsis orientalis

<400> SEQUENCE: 3
atgaaactga gcggcgtgga actgcggcga gtccggatgc cgctcgtggc cccgttccgg     60
acgtcgttcg ggacgcagtc cgagcgggaa ttgctgctgg tccgcgcggt gaccccggcg    120
```

-continued

```
ggcgagggct gggcgaatg tgtcgcgatg gaggcgccgc tctactcgtc ggagtacaac      180
gacgccgccg agcacgtgct gcggaaccat ctgatcccg cactgctggc ggccgaggac      240
gtgaccgcgc acaaggtgac gccgttgctg gcgaagttca agggccaccg gatggcgaag    300
ggcgcgctgg agatggcggt cctcgacgcc gaactccgcg cgcatgaccg gtccttcgcg    360
gccgagctgg ggtccactcg cgactccgtg gcctgcgggg tctcggtcgg gatcatggac    420
tcgatcccgc acctgctcga cgtcgtcggc ggctacctcg acgagggcta cgtccgcatc    480
aagctcaaga tcgaacccgg ctgg                                           504
```

```
<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 4
atgaaactga gcggcgtgga actgcggcga                                      30

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 5
ctcatcaagc tcaagatcga accccggctg g                                    31

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 6
gaattcgtaa gatcttacga accgatccac g                                    31

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 7
caaggagcac atatgaaact cagcggtgtg g                                    31
```

N-ACETYL AMINO ACID RACEMASE

BACKGROUND OF THE INVENTION

1. Field of the Invention

The present invention is directed at an N-acetyl amino acid racemase (AAR) from *Amycolatopsis orientalis* subspecies lurida, as well as the gene coding for it, and at plasmids, vectors, and microorganisms containing the gene.

2. Discussion of the Background

Using N-acetyl amino acid racemases, it is possible to obtain optically pure amino acids at a yield of 100% from the corresponding protected racemic N-acetyl amino acids, in interaction with acylases. Optically pure amino acids are used in parenteral feeding as well as for the production of chiral bioactive substances.

N-acetyl amino acid racemases (AAR) from *Streptomyces atratus* Y-53 (Tokuyama et al, *Appl. Microbiol. Biotechnol.* 1994, 40, 835–840) and *Amycolatopsis* sp. TS-1-60 (Tokuyama et al., *Appl. Microbiol. Biotechnol.* 1995a, 42, 853–859) are already known.

The AAR from *Amycolatopsis* sp. TS-1-60 has a strong dependence on cobalt and manganese ions with regard to its activity. The addition of these heavy metal ions to the synthesis stock is a disadvantage on a large technical scale, from the aspect of environmental protection.

BRIEF SUMMARY OF THE INVENTION

It is an object of the present invention to provide an AAR that has a lesser activity dependence on heavy metal ions, as compared with the AAR from *Amycolatopsis* TS-1-60.

Another object of the invention to provide a gene coding for this enzyme.

Another object of the invention to provide a plasmid, vecor and microorganism that contain the AAR gene.

Another object of the invention to provide a primer for the AAR gene.

Another object of the invention to provide a gene probe for detecting the AAR gene.

Another object of the invention is to provide a process for producing enantiomer-enriched amino acids. BRIEF DESCRIPTION OF THE DRAWINGS A more complete appreciation of the invention and many of the attendant advantages thereof will be readily obtained as the same becomes better understood by reference to the following Figures in conjunction with the detailed description below.

DETAILED DESCRIPTION OF THE INVENTION

Because the N-acetyl amino acid racemase (SEQ ID NO: 2) from *Amycolatopsis orientalis* subspecies lurida is made available for the racemization of N-acetyl amino acids, an enzyme is obtained that racemizes exclusively N-acetyl amino acids, does not convert N-unprotected amino acids, and furthermore demonstrates a lesser dependence on the heavy metal ion $Co^{2+}$. This fact is extremely advantageous for large-scale technical use of the enzyme, from cost and environmental aspects. The identity on a DNA level of *Amycolatopsis* sp. TS-1-60 (Tokuyama et al., *Appl. Microbiol. Biotechnol.* 1995b, 42, 884–889) and *A. orientalis* subspecies lurida with regard to the gene that codes for the racemase is 86%. It was therefore very surprising to find the same enzymes with such different properties in a species of microorganisms.

In another embodiment of the invention, a gene (SEQ ID NO.: 1) coding for the racemase according to the invention is claimed. According to the invention, this also includes those genes that appear possible within the scope of the band width that is predetermined by the degeneration of the genetic code.

Figure 3:
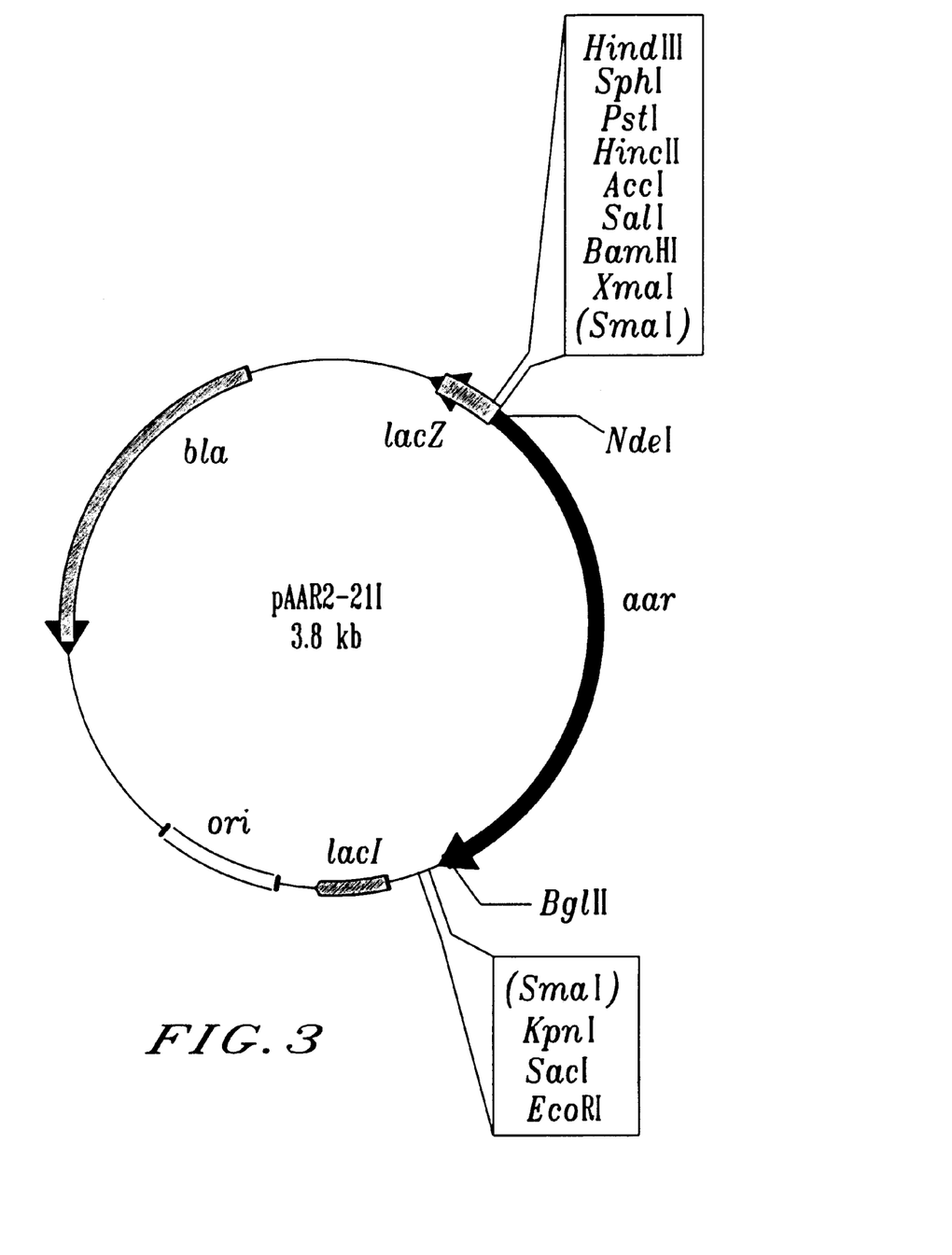
FIG. 3: Plasmid pAAR2-21I.
Figure 4:
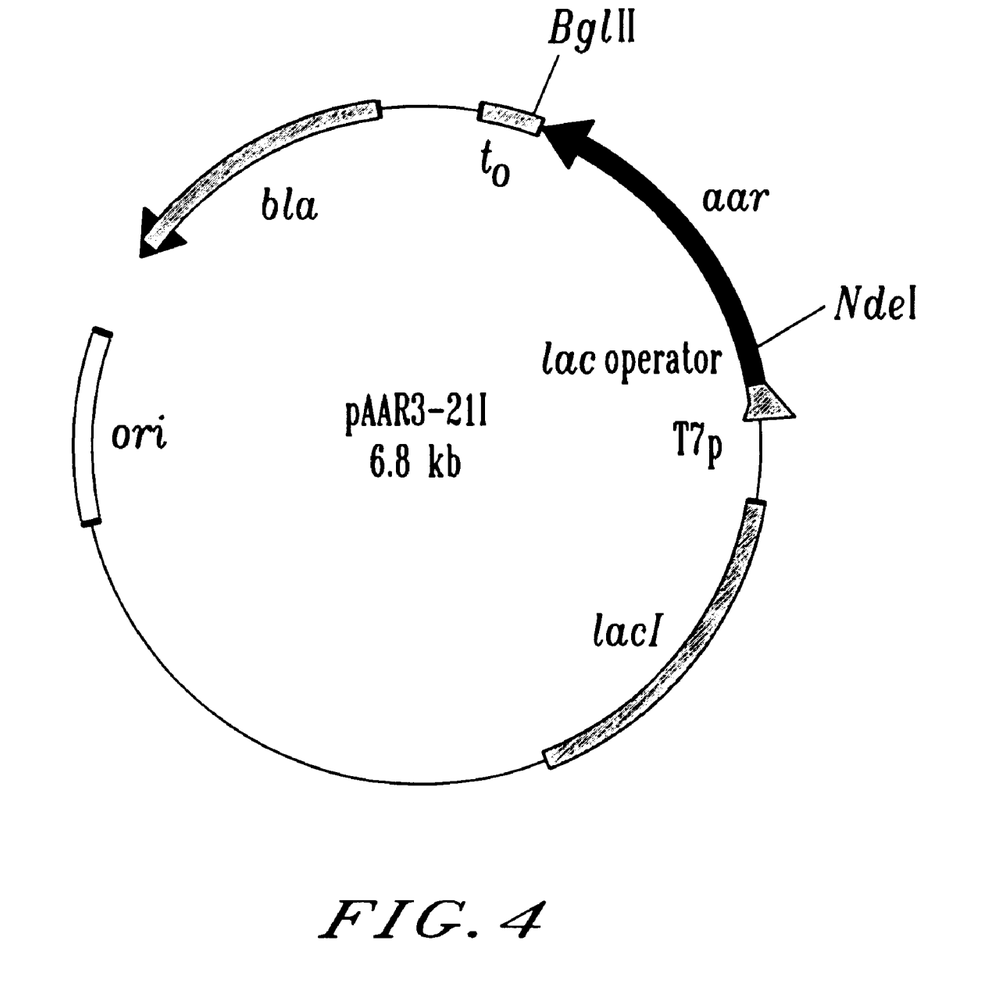
FIG. 4: Plasmid pAAR3-21I.

Furthermore, within the scope of the invention, plasmids or vectors that demonstrate the genes according to the invention are also protected. pAAR1-21I, pAAR2-21I, and pAAR3-21I (FIGS. 1, 3, and 4) should be viewed as preferred plasmids and vectors.

In another embodiment of the invention, all microorganisms that demonstrate the genes according to the invention are claimed. In particular, these are microorganisms such as the *E. coli* strains (DH5α and/or BL21) that carry the plasmid. In this connection, strain DE3 is very especially preferred. The selection of a microorganism suitable for use in the invention is within the level of skill of those of ordinary skill in the art, without undue experimentation.

Fundamentally, any plasmid (vector)/host system known to a person skilled in the art, in which the gene can be cloned via a corresponding interface, i.e. the construct formed in this way can be transformed, can be used for implementing the invention. The preparation of these plasmid (vector)/host systems is within the level of skill of those of ordinary skill in the art, without undue experimentation. An overview of the T7 expression system is given in Studier et al., *Methods Enzymol.* 1990, 185, 61–69. Other suitable expression systems can be found in the relevant known brochures from the Novagen, Promega, New England Biolabs, Clontech, as well as Gibco BRL companies.

The derivation of suitable primer takes place by means of a comparison of DNA sequences of the gene being searched for that are already known, or by "translation" of amino acid sequences into the codon use of the corresponding organism (for example, for Streptomycetes: Wright et al., *Gene*, 1992, 113, 55–65). Coinciding amino acid sequences of proteins from so-called superfamilies are also helpful in this connection (Firestine et al., *Chemistry & Biology*, 1996, 3, 779–783).

In this connection, the AAR mentioned here belongs to the enolase superfamily (Babbit et al., *Biochemistry* 1996, 35, 16589–16501). The preparation of primers suitable for use in the invention is within the level of skill of those of ordinary skill in the art, without undue experimentation. In particularly, two primers (AR1) and (AR5) can be constructed for successful PCR-mediated amplification of a gene segment.

AR1: 5' ATG AAA CTG AGC GGC GTG AAA CTG CGG CGA 3' (SEQ ID NO: 4)

AR5: 5-CCA GCC GGG TTC GAT CTT GAG CTT GAT GCG 3' (SEQ ID NO: 5)

Furthermore, the initial and end sequences of the gene according to the invention, which carry the interface, should be viewed as preferred primers. Suitable interfaces can be found in the brochures indicated above.

The following sequences, which demonstrate the NdeI or BglII interface, are very especially preferred:

AR_Ex1Nde: 5'CAA GGA GCA CAT ATG AAA CTC AGC GGT GTG G3' (SEQ ID NO: 6)

AR_Ex2Bgl: 5'GAA TTC GTA AGA TCT TAC GAA CCG ATC CAC G3' (SEQ ID NO: 7)

A fragment of the gene according to the invention, with a size of 504 bp, was amplified using the two primers AR1 and AR5. This technique is discussed in detail in Saiki et al., Science (1988), 239, 487–491, and therefore known to those skilled in the art. Its sequence of base pairs (SEQ ID NO: 3) is represented as follows below:

5'ATGAAACTGAGCGGCGTGGAACTGCGGC-
GAGTCCGGATGCCGCTCOTGGCCCCGTTC
CGGACGTCGTTCGGGACGCAGTC-
CGAGCGGGAATTGCTGCTGGTCCGCGCG-
GTGACCCC GGCGGGCGAGGGCTGGGGCGAAT-
GTGTCGCGATGGAGGCGCCGCTCTACTCGTC
GGAGT
ACAACGACV7CCGCCGACCACGTGCTGCGGA
ACCATCTGATCCCCGCACTGCTGGCGGCC
GAGGACGTGACCGCGCACAAGGTGACOC-
CGTTGCTGGCGAAGTTCAAGGGCCACCGGAT
GGCGAAGGGCGCGCTGGAGATGGCGGTC-
CTCOACGCCGAACTCCGCGCGCATGACCGGT
CCTTCGCGGCCGAGCTGGGGTC-
CACTCGCGACTCCGTGGCCT-
GCGGGGTCTCGGTCGGG ATCATGGACTC-
GATCCCGCACCTGCTCOACGTCGTCGGCGGC
TACCTCGACGAGGGCTA CGTCCGCATCAAGCT-
CAAGATCGAACCCGGCTGG3'

It serves as part of a probe to find the claimed gene. The production of a gene probe from a gene fragment is presented in Sambrook et al., A laboratory manual, Cold Spring Harbor Laboratory Press, New York (1989), among other references, and is within the level of skill of those of ordinary skill in the art, without undue experimentation. In this special case, the aforementioned gene fragment was used together with the DIG marking of Roche Diagnostics.

An object of the present invention is also the use of the racemase according to the invention in a process for the production of optically enriched amino acids or their derivatives. For this purpose, the racemic N-acetyl amino acid is brought to reaction in the presence of an acylase and the AAR, under physiological conditions, and by conventional methods known to those of ordinary skill in the art. Because the amino acid that is formed is removed from the equilibrium of the reaction by precipitation, and the AAR from the remaining optically enriched N-acetyl amino acid always forms the racemate, 100% conversion of the racemate to an optical antipode of the amino acid in question takes place.

Preferably, this process takes place in an enzyme membrane reactor (DE 199 10 691.6).

Using the probe discussed above, an EcoRI fragment of genomic DNA of A. orientalis subspecies lurida, with a size of approximately 2.5 kb, was detected using Southern hybridization (Sambrook et al., A laboratory manual, Cold Spring Harbor Laboratory Press, New York (1989), and Hopwood et al., A laboratory manual, The John Innes Foundation, Norwich (1985)).

Shot-gun cloning followed, in which the entire DNA population of EcoRI fragments of the genomic DNA, with a size of 2.5 kb, were ligated into the plasmids pUC18 (Vieira et al., Gene (1982), 19, 259–268), which had previously been hydrolyzed with the restriction enzyme EcoRI.

The vectors obtained in this way were then transformed in E. coli DHSU. Identification of the DNA fragment with the gene of the AAR then took place by means of colony hybridization (Sambrook et al., A laboratory manual, Cold Spring Harbor Laboratory Press, New York (1989), and Hopwood et al., A laboratory manual, The John Innes Foundation, Norwich (1985)), using the DIG-marked 504 bp probe described above.

Figure 1:
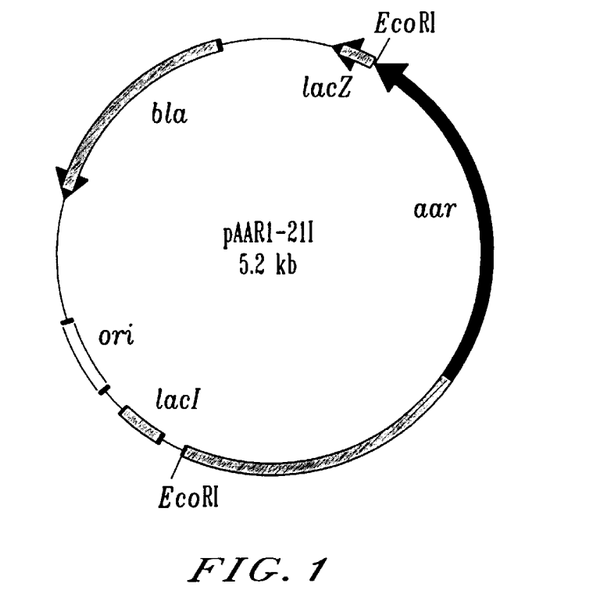
FIG. 1: Plasmid pAAR1-21I.
Figure 2:
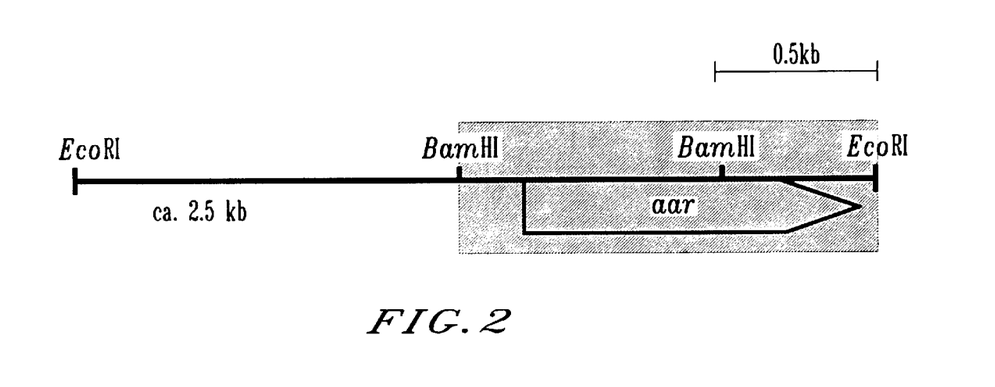
FIG. 2: Restriction card of the 2.5 kb EcoR1 fragment with the AAR gene.

The plasmid obtained, with the AAR gene, was called pAAR1-21I (FIG. 1). FIG. 2 shows the restriction card of the 2.5 kb EcoRI fragment with the AAR gene. The 1.3 kb EcoRI fragment with the AAR gene was sequenced in the double strand and analyzed.

The primers AR_Ex1Nde and AR_Ex2Bgl were used for amplification of the entire gene from pAAR1-21I, using PCR. Using these primers, an NdeI restriction interface was inserted at the 5' end of the gene, and a BglII interface was inserted at the 3' end of the AAR gene.

The amplificate was ligated blunt-end into plasmid pUC18, hydrolyzed with SmaI, and the construct pAAR2-21I (FIG. 3) obtained in this way was transformed in E. coli DHSα.

The insertion of these restriction interfaces NdeI and BglII allowed cloning of the gene in the expression vector pET11a (Novagen). This expression vector, called pAAR3-21I (FIG. 4), with the AAR gene from A. orientalis subspecies lurida, was transformed in the expression strain E. coli BL21 (DE3) (Novagen; contains T7 polymerase, integrated into the genome under the control of the lac operator).

Using the expression plasmid pAAR3-21I, it was possible to superexpress the AAR from the A. orientalis subspecies lurida in E. coli BL21 (DE3) heterologously, according to a modified protocol of Studier et al., Methods. Enzymol. (1990), 185, 61–89). The superexpression was induced by isopropyl thiogalactoside (IPTG). The E. coli expression strain originally did not possess any N-acetyl amino acid racemase activity.

The AAR activity was followed up in a coupled enzymatic assay (Diagram 1), in that the formation of a deacetylated amino acid from an N-acetyl-D-amino acid, methionine here, was detected using the HPLC system I. The L-specific amylases from pig kidneys or Aspergillus oryzae served as the auxiliary enzymes.

Diagram 1: Schematic representation of the enzyme assay.

Purification of the heterologously superexpressed AAR took place via three steps, after cell digestion:

1. Heat precipitation at 50° C. for 30 min.
2. Anion exchange chromatography via Q-sepharose (fast flow; Pharmacia).
3. Hydrophobic interaction chromatography via phenyl sepharose (stream line; Pharmacia).

Further characterization of the AAR took place using the HPLC system II. Using this system, it was possible to study the activity of the AAR directly. In this way, it was possible to do without the auxiliary enzyme, the acylase, so that it was possible to avoid disruptive interference activity.

Figure 5:
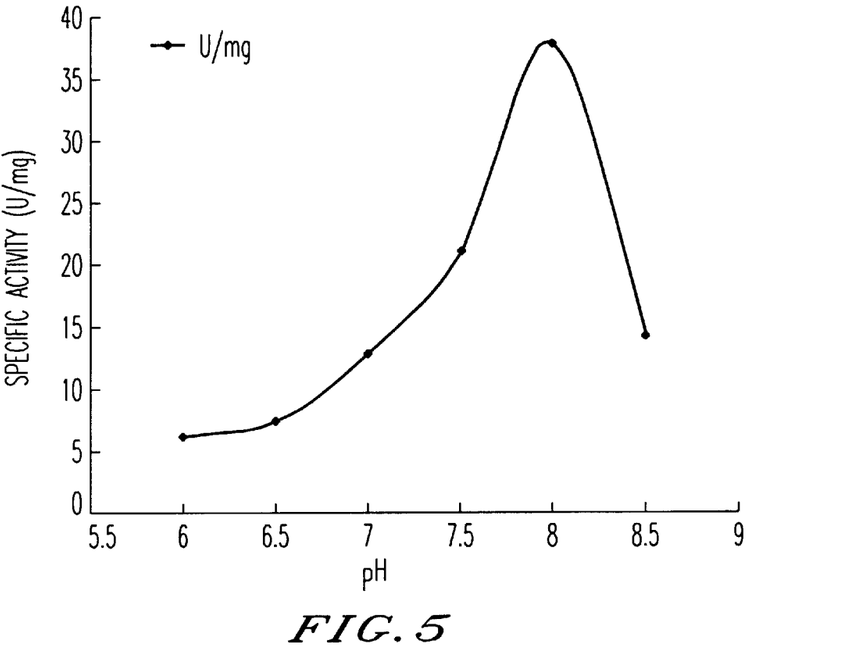
FIG. 5: Effect of pH on AAR activity.
Figure 6:
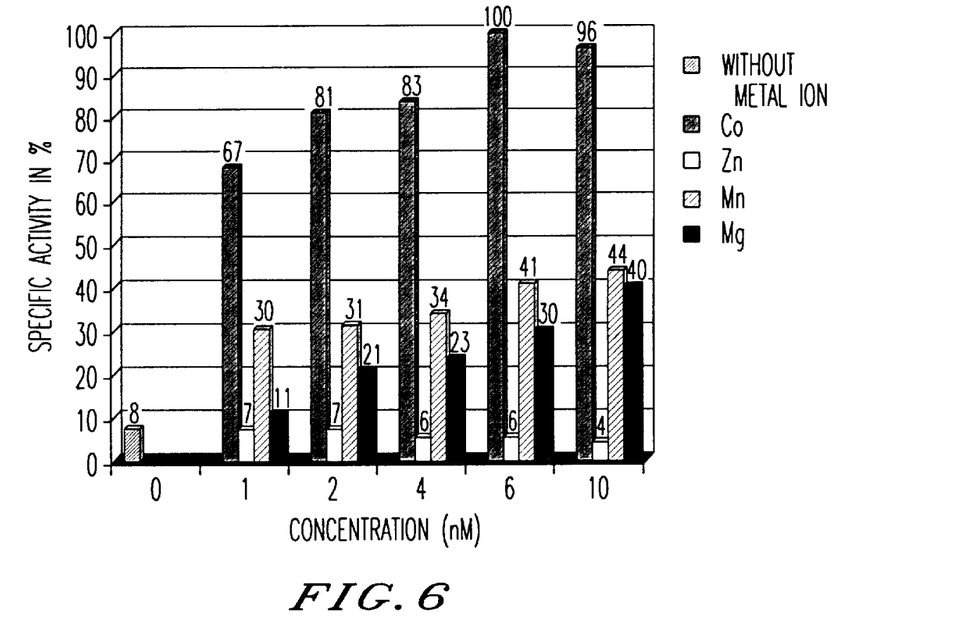
FIG. 6: Effect of $Co^{2+}$, $Zn^{2+}$, $Mn^{2+}$ and $Mg^{2+}$ concentration on AAR activity.
Figure 7:
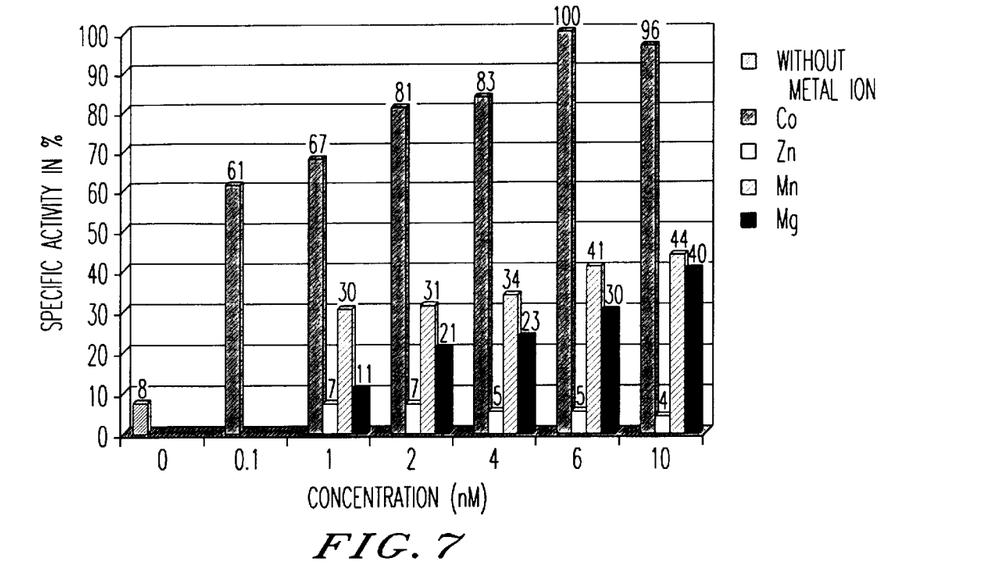
FIG. 7: Effect of $Co^{2+}$, $Zn^{2+}$, $Mn^{2+}$ and $Mg^{2+}$ concentration on AAR activity.
Figure 8:
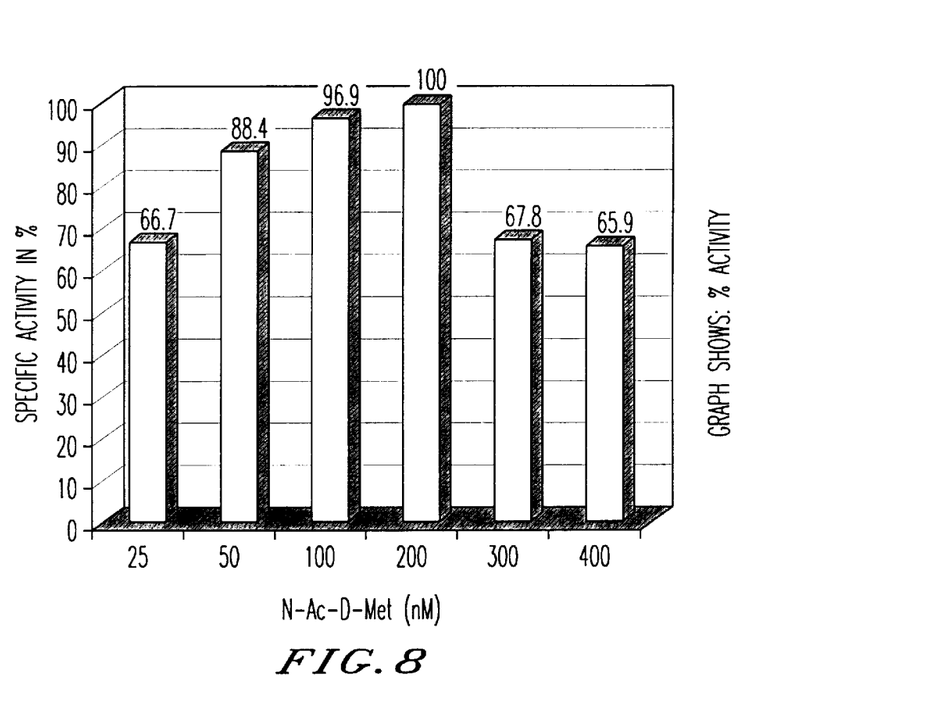
FIG. 8: Effect of N-acetyl-D-methionine concentration on AAR activity.

The following properties of AAR from A. orientalis subspecies lurida have crystallized out:

i) AAR exclusively racemizes N-acetyl amino acids, while amino acids not protected with N-acetyl are not converted.

ii) The superexpressed protein band of the AAR appears in SDS-PAGE analysis (Laemmli, Nature (1970), 227, 680–685), in the denatured state, at a molecular weight of approximately 409 kDa.

iii) The AAR possesses an optimum pH at pH 8 (FIG. 5).

iv) The specific AAR activity after purification was 30.6 U/mg with 2 mM $CoCl_2 \times 6H_2O$ in the assay. This value is therefore approximately 30.8% higher than the one found for racemase by Tokuyama and Hatano (Appl. Microbiol. Biotechnol. 1996, 44, pp. 774–777).

v) The activity with 10 mM $CoCl_2 \times 6H_2O$ in the assay was 37.5 U/mg.

vi) The increase in the activity of the AAR from *A. orientalis* subspecies lurida at 1 mM $CoCl_2 \times 6H_2O$ as compared with the activity without metal ion in the assay was 1250%. The addition of 1 mM $CoCl_2 \times 6H_2O$ in the assay resulted in an increase of only 496% for the AAR from A. sp. TS-1-60 (Tokuyama and Hatano, *Appl. Microbiol. Biotechnol.* 1996, 44, 774–777). This shows that the AAR from *A. orientalis* subspecies lurida is 152% more active than the racemase from A. sp. TS-1-60, with the same $CoCl_2 \times 6H_2O$ concentration in the assay.

vii) Other bivalent ions, such as $MnCl_2 \times 4H_2O$, $ZnSO_4 \times 7H_2O$, and $MgCl_2 \times 6H_2O$, were tested in various concentrations, in the standard enzyme assay. In this connection, Mn and Mg still demonstrated about 40% of the activity, at 10 mM, in comparison with cobalt substitution (FIG. 6).

viii) Substrate inhibition occurs in the AAR from *A. orientalis* subspecies lurida at substrate concentrations of N-acetyl-D-methionine greater than 200 mM (FIG. 7). For TS-1-60, inhibition was already observed at 50 mM N-acetyl-D-methionine.

It can be stated that the present racemase makes available clear advantages as compared with the one mentioned from the state of the art, in terms of activity, heavy metal ion dependence, and inhibition tendency, for use on an industrial scale.

The microorganism *Amycolatopsis orientalis* subspecies lurida is filed with the Deutsche Sammlung für Mikroorganismen [German Collection for Microorganisms] under the number DSM43134.

Within the scope of the invention, AAR is understood to mean both the natural enzyme and the enzyme produced by recombinant technology.

Having generally described this invention, a further understanding can by obtained by referenced to certain specific examples which are provided herein for purposes of illustration only and are not intended to be limiting unless otherwise specified.

EXAMPLES

Example 1

Raising the Actinomycete strain *Amycolatopsis orientalis* subspecies lurida, and Preparation of the Genomic DNA The actinomycete strain *Amycolatopsis orientalis* subsp. lurida (DSM43134) grew on TSB medium (Oxoid, Wesel). The culture was washed with sterile 10.3% saccharose solution twice after harvesting, and stored at −20° C. until use. Preparation of the genomic DNA took place according to Mehling et al., *FEMS Microbiol. Lett.* (1995), 128, 119–126.

Example 2

Oligonucleotides

TABLE 1

List of oligonucleotides used:

| Designation: | Use: | Sequence: |
|---|---|---|
| AR1 | PCR | 5' (AG) TG AA(AG) CT(GC) AG(GC) GG(GCT) GT(GC) GA(AG) CT(GC) CG(GC) |

TABLE 1-continued

List of oligonucleotides used:

| Designation: | Use: | Sequence: |
|---|---|---|
| AR5 | PCR | CGA3 5' CCA (GC)CC (GC)GG (GCT)TC GAT CTT (GC)AG CTT GAT (GC)CG 3' |
| AR_Ex1Nde | PCR | 5' CAA GGA GCA CAT ATG AAA CTC AGC GGT GTG G 3' |
| AR_Ex2Bgl | PCR | 5' GAA TTC GTA AGA TCT TAC GAA CCG ATC CAC G 3 |

Example 3

Gene Technology Methods

All of the gene technology methods used here are described by Sambrook et al., *A laboratory manual*, Cold Spring Harbor Laboratory Press, New York (1989), and Hopwood et al., *A laboratory manual*, The John Innes Foundation, Norwich (1985), unless noted otherwise, and are well known to those skilled in the art. All of the enzymes and corresponding buffers were used in accordance with the manufacturers' information. Cy5 marked primer was used for automatic sequencing with the ALFred DNA Sequencer (Pharmacia, Freiburg). The Southern blot and hybridization, as well as 3'-DIG labeling (for nonradioactive detection) of the DNA probes took place according to information from Roche Diagnostics.

Example 4

Polymerase Chain Reaction (PCR)

DNA amplification by means of the polymerase chain reaction was carried out using the Biometra Thermocycler (Göttingen), analogous to Saiki et al., *Science* (1988), 239, 487–491, a technique known to those or ordinary skill in the art. Genomic DNA from *A. orientalis* subspecies lurida served as the template. The thermostable DNA polymerase Taq (Gibco BRL) was used in the PCR batches. The primer pairs used are listed in Table 1. The annealing temperature A was determined via the DNA melt temperature ($T_m$) of the oligonucleotides. The time X for the chain reaction of the DNA polymerase was based on the 1 kb=1 min rule. All the batches were coated with approximately 50 μl mineral oil.

| Composition of the PCR batch: |
|---|
| Polymerase buffer (10 × 5 μl) |
| dNTPs, 10 nmol each |
| Primers, 50 pmol each |
| DMSO 10% |
| DNA polymerase 1 U |
| Chromosomal DANN 10–100 ng |
| Fill up with $H_2O$ to 50 μl |
| ($MgCl_2$ according to information from the polymerase manufacturer) |

| Amplification Program: | | |
|---|---|---|
| Step 1 | 98° C. | 5 min. |
| 2 | 95° C. | 1 min. |
| 3 | A° C. | 45 sec |

-continued

Amplification Program:

| 4 | 72° C. | Xmin. |
| 5 | 72° C. | 2 min. | addition of DNA polymerase at Step 2, Steps 2–4 were run through 30 times.

TABLE 2

List of the primer pairs used for the PCR (cf. Table 1), annealing temperatures, as well as the length of the amplificates.

| Primer pair: | Annealing temperature ($T_m$): | Length of the DNA to be amplified: |
|---|---|---|
| AR1/AR5 | 73.8° C. | 1.1 kb |
| AR_Ex1Nde/AR_Ex2Bgl | 69.0° C. | 1.1 kb |

Example 5

Hybridization According to Southern, and Colony Hybridization

For hybridization according to Southern, aliquots of preparations of the genomic DNA of *A. orientalis* subspecies lurida were hydrolyzed with the restriction enzyme EcoRI. The resulting DNA fragments were then separated via an agarose gel. The fragments separated in this way were subsequently blotted on a nylon membrane (Hybond N+, Amersham). The DIG-marked (Roche Diagnostics) 504 bp fragment of *A. orientalis* subspecies lurida was used as a probe. The hybridization temperature was 61° C.

The 2.5 kb DNA fragment of *A. orientalis* subspecies lurida that gave off the signal was eluted, ligated with the EcoRI hydrolyzed plasmid pUC18, and subsequently shot-gun cloned in *E. coli* DH5α.

The *E. coli* transformants obtained by shot-gun cloning were spread onto $LB_{amp100}$ plates, at 50 each. Using these plates, a colony lift and then colony hybridization was performed. Again, the DIG-marked 504 bp fragment of *A. orientalis* subspecies lurida served as the probe. Using this method, it was possible to clearly identify an *E. coil* transformant with the AAR gene. The plasmid was called pAAR1-21I.

These techniques are discussed in detail in Sambrook et al., *A laboratory manual*, Cold Spring Harbor Laboratory Press, New York (1989), and Hopwood et al., *A laboratory manual*, The John Innes Foundation, Norwich (1985), and therefore known to a person skilled in the art.

Example 6

Heterologous Expression of the AAR Enzyme from *A. orientalis* Subspecies Lurida in *E. coil* BL21 (DE3)

Standardized heterologous expression of the recombinant AAR enzyme from *A. orientalis* subspecies lurida in *E. coli* BL21 (DE3) took place analogous to Studier et al., *Methods Enzymol.* 1990, 185, 61–89:

*E. coli* BL21 (DE3) derivatives transformed with plasmids for superexpression (pAAR3-21I) were incubated in LB medium (with 100 µg/ml ampicillin), overnight (ÜN), at 37° C. Then 500 ml main culture (LB medium with 100 µg/ml ampicillin in 4 baffle plate flasks) were inoculated with 10 ml overnight culture (1:50). The T7 polymerase was induced at a cell density of $OD_{600nm}$=0.5–0.9, with 5 ml of a 100 mM IPTG solution (concentration in flask 1 mM; IPTG=isopropyl thiogalactoside). After another 4–6 h incubation at 37° C., the cells were harvested.

In crude extracts of the expression clone, which were raised in the manner described above, it was possible to determine an AAR activity of 0.6–1.2 U/mg total protein.

Example 7

Detection of Racemase Activity of the Recombinant AAR Enzyme

Crude extracts of the superexpression clone, i.e. purified enzyme fractions, were used in an enzyme test, in that it was possible to detect the formation of L-methionine from N-acetyl-D-methionine (see Diagram 1), via HPLC:

The standard enzyme test (modified according to Tokuyama et al., *Appl. Microbiol. Biotechnol.* (1994), 40, 835–840; ibid., *Appl. Microbiol. Biotechnol.* (1995a), 42, 853–859), was composed as follows:

Solvent: Tris/HCl, pH 7.5, 50 mM

N-acetyl-D-methionine 25 mM

Cobalt chloride 2 mM

Acylase I (ASch or AAsp) 1 U

Protein 2–150 µg purified protein or total protein

End volume 200 µl

In this connection, acylase I and $Co^{2+}$ are present in excess, so that the AAR reaction is the step that determines the speed. Incubation took place for 10–40 min at 30° C. The reaction was then stopped by boiling for 3 min. Analysis of the reaction products took place using HPLC (System I).

Unless mentioned otherwise, acylase I from pig kidneys (ASch) was used in the enzyme test, and $Co^{2+}$, was used as the ion ($CoCl_2 \times 6H_2O$). Alternatively, however, acylase I from *Aspergillus oryzae* (AAsp) was also used.

In assays that were analyzed using the HPLC system II, the acylase could be left out, since it is possible to separate and analyze N-acetyl amino acids directly, enantioselectively, with this system.

Other than $Co^{2+}$ ($CoCl_2 \times 6H_2O$), other bivalent ions, such as $MnCl_2 \times 4H_2O$, $SO_4 \times 7H_2O$, and $MgCl_2 \times 6H_2O$ were used in various concentrations (0.1–10 mM).

Substrate inhibition was tested in that the activity of the AAR was mixed with 25 to 400 mM N-acetyl-D-methionine as the substrate.

Example 8

HPLC Analysis

System I:

Column: RP C 18, 5 µm, 250×4.6 mm, Chromasil®

Flow agent A: 23 mM sodium acetate, 10% acetonitrile, pH 6.0

Flow agent B: 100% acetonitrile

Flow rate: 1 ml/min

Sample volume: 20 µl

Detection: UV-VIS 225 nm

Fluorescence: 340/440 nm

Derivativization: on the basis of o-phthaldialdehyde (OPA)/N-isobutyryl-L-cysteine (IBLC) according to Brückner et al., *Journal of Chromatography* A (1994), 666, 259–273.

| Gradient: | |
|---|---|
| Time | Mixture |
| 0 min. | 0% B |
| 20 min. | 24% B |
| 22 min. | 100% B |
| 23 min. | 100% B |
| 25 min. | 0% B |
| 35 min. | 0% B |

System II:
 Column: ENAN 1, Merget, 145×4.6 mm, (Dr. K. Günther, Degussa-Hüls AG, lent by him personally)
 Flow agent A: 700 ml methanol, 300 ml ammonium acetate (0.01 M), 0.5 ml pure acetic acid
 Flow rate: 1 ml/min
 Sample volume: 20 μl
 Detection: UV-VIS 225 nm
 Gradient: isocratic

Example 9

Purification of the AAR from *A. orientalis* Subspecies Lurida

Purification of the heterologously superexpressed AAR took place via three steps, after cell digestion:

1. Cell digestion: 30% cell suspension with Tris/HCl (pH 7.5) and 1.5 times the amount of glass beads (diameter 0.3 mm) were mixed and digested in the disintegrator S (for 2 times 15 min).

2. Heat precipitation at 50° C. for 30 min.

3. Anion exchange chromatography via Q-sepharose (fast flow; Pharmacia), elution at approximately 25% flow agent B.

3. Hydrophobic interaction chromatography via phenyl sepharose (stream line; Pharmacia), elution at approximately 40% flow agent B. Elution took place, in each instance, with 50 mM Tris/HCl, pH 7.5 (flow agent A), via a linear gradient, with 0.5 M $(NH_4)SO_4$ in 50 mM Tris/HCl, pH 7.5 (flow agent B).

The entire disclosure of German Patent Application No. 199 35 268.2, filed on Jul. 27, 1999, including specification, FIGS. 1–8, Claims, and Abstract are incorporated herein by reference in its entirety.

Obviously, numerous modifications and variations of the present invention are possible in light of the above teachings. It is therefore to be understood that within the scope of the appended claims, the invention may be practiced otherwise than as specifically described herein.

---

We claim:

1. An isolated N-acetyl amino acid racemase comprising the amino acid sequence shown in SEQ ID NO: 2.

2. The N-acetyl amino acid racemase of claim 1 which is isolated from *Amycolatopsis orientalis* subspecies lurida.

3. A process for producing an enantiomer-enriched amino acid compound, derivative thereof, which process comprises incubating a racemic mixture of a N-acetyl amino acid with a N-acetyl amino acid racemase having the amino acid sequence shown in SEQ ID NO: 2, and isolating the enantiomer-enriched amino acid compound.

4. The process of claim 3 wherein the reaction is carried out in an enzyme membrane reactor.

5. The process of claim 3 which further comprises adding acylase to the racemic mixture of a N-acetyl amino acid with a N-acetyl amino acid racemase.

* * * * *